United States Patent [19]

Hon et al.

[11] Patent Number: 4,944,307

[45] Date of Patent: Jul. 31, 1990

[54] INTRAUTERINE CATHETER

[75] Inventors: Edward H. Hon, Bradbury; Robert W. Hon, Los Altos; Edward D. Hon, San Francisco, all of Calif.

[73] Assignee: The Hon Group, Encino, Calif.

[21] Appl. No.: 234,546

[22] Filed: Aug. 22, 1988

[51] Int. Cl.⁵ ............................................. A61B 5/03
[52] U.S. Cl. ................................... 128/748; 128/778; 128/775
[58] Field of Search .................... 128/748, 774–775, 128/778, 780, 672–675, 341–344; 604/101–104

[56] References Cited

U.S. PATENT DOCUMENTS

| | | | |
|---|---|---|---|
| 3,752,150 | 8/1973 | Harris | 128/778 |
| 4,048,985 | 9/1977 | Sasse | 128/778 |
| 4,136,681 | 1/1979 | Hon | 128/748 |
| 4,216,783 | 8/1980 | Kaiser et al. | 128/748 X |
| 4,252,131 | 2/1981 | Hon et al. | 128/748 |
| 4,325,387 | 4/1982 | Helfer | 128/748 |
| 4,543,965 | 10/1985 | Pack et al. | 128/774 X |

*Primary Examiner*—Angela D. Sykes
*Attorney, Agent, or Firm*—Lewis Anten

[57] ABSTRACT

An intrauterine catheter is disclosed employing a catheter tube closed at one end by a flexible membrane, and connected at its other end to the input of a pressure transducer. The catheter is filled by injection of a sterile solution through the flexible membrane into the catheter tube or by pre-filling. The pressure measuring system is capable of being zeroed while the catheter is in place in the uterus.

32 Claims, 5 Drawing Sheets

INTRAUTERINE CATHETER

BACKGROUND OF INVENTION

This invention concerns the measurement of intrauterine pressure and more specifically to a intrauterine catheter adapted for the measurement of intrauterine pressure during labor.

Fetal monitoring is a standard procedure for monitoring the condition of a fetus during childbirth. In most cases fetal heart rate and intrauterine pressure are measured and separately plotted on a strip-chart recorder. By examining these curves, the onset of certain distress conditions can be detected so that appropriate remedial action can be taken earlier than would otherwise be possible.

At present, to measure intrauterine pressure, an open-ended liquid filled catheter is inserted into the uterus so that the force of the intrauterine contractions can be transmitted through the uterine fluids and the liquid in the catheter to a pressure measuring device such as a strain gauge or the like.

In prior art applications of the type described, a cumbersome procedure is required to fill the catheter with liquid and then to couple the catheter to the strain gauge or the like to complete a liquid path or column from the uterus to the gauge.

Conventionally, the catheter is inserted through a relatively rigid guide tube which is curved to conform to the vaginal canal. The catheter is pushed through the guide tube until the uterine end of the catheter tube is located correctly within the uterus.

The catheter tube is coupled by means of an adaptor to a three-way stopcock, with two inlets of the stopcock being connected, respectively, to the lower fitting of the strain gauge and the syringe. The third inlet is "open to air". This enables the operator to open the system "to air" to check the electrical zero, i.e. "0" millimeters of mercury at any time during the recording to provide a means of calibrating the recorded data. This is accomplished by turning the "off" lever on the stopcock to the "open to air" inlet. The electrical zero can then be adjusted to "0" if necessary. The "off" lever is then turned towards the liquid filled syringe and liquid is injected into the system to purge any air from it and fill it again with liquid. The "off" lever is then turned towards the strain gauge closing the system.

During such an operation, if the "off" lever of the stopcock is improperly rotated, the force generated by the advancing syringe plunger may be applied directly against the transducer diaphragm, damaging it.

During use, presently available intrauterine catheters of the type described may have their openings "plugged" by clotted blood or other biologic debris present within the uterus. If this happens, pressure measurements are compromised and the catheter must be flushed to remove the debris and the system again bled as described above. If this is not successful, the catheter must be replaced.

Despite the use of a sterile liquid, because the liquid injection and air bleeding procedures take place in a non sterile environment, use of these standard catheters too frequently is accompanied by substantial risk of infection.

Other devices have been devised to avoid such a cumbersome procedure, including the invention of the co-applicants, Edward H. Hon, M.D., U.S. Pat. No. 4,136,681. In the device described therein, a catheter is disclosed for measuring the intrauterine pressure of a woman in labor. It comprises an elongated flexible tube which is inserted into the uterus through a curved guide tube adapted to be inserted through the vagina and cervix of a woman in labor. The catheter tube contains a sterile liquid and is closed at both ends by a seal which is capable of transmitting pressure from the liquid within the catheter to an external liquid. In a preferred embodiment, a limp membrane is used to couple the catheter tube to a strain gauge or the like for measuring pressure. The catheter end within the uterus includes a number of pinholes and a capillary material within the tube to prevent loss of the catheter liquid. Alternatively, and particularly where it is desired not to rupture the amniotic membrane, a second limp membrane may be used as the means for coupling between the catheter liquid and the uterus.

The use of the limp membrane at the uterine end of the catheter tube was found to be unacceptable due to the fact that during use it would frequently fold over itself, bend, or break due to the tension placed on it during insertion into the uterus.

Recently, disposable intrauterine catheters have been introduced, such as from Utah Medical, Inc., where a miniature transducer is placed on the catheter tip. (These are costly and represent a departure from the tried and true apparatus for measuring contraction.) Such devices have relatively large tips and are supported by relatively rigid wires which may cause damage to the fetus and uterine walls. Additionally, since the catheter is unprotected from its entrance to the vagina, until it is placed high in the uterus, the probability of transporting infectious material inside the uterus is high; the insertion of the large tip pushes bacteria high into the uterus where it is more likely to cause infection.

Also, in order to check the operations of such devices, once in place in the uterus, it is necessary to remove the catheter. This is highly undesirable, since it raises the probability of additional infection as well as being inconvenient and time-consuming.

OBJECTS OF THE PRESENT INVENTION

It is an object of the present invention to provide an improved intrauterine catheter which is easier to use than presently available catheters.

It is also an object of the present invention to provide an improved intrauterine catheter which is easier to fill or may be pre-filled.

It is also an object of the present invention to provide an improved intrauterine catheter which may be more easily connected to monitoring equipment.

It is also an object of the present invention to provide an improved intrauterine catheter which is more economical.

It is yet another object of the present invention to provide an improved intrauterine catheter which reduces the risk of infection or contamination during use.

It is yet another object of the present invention to provide an improved accessory for existing catheter tubes.

It is yet another object to provide an improved catheter device that may be zeroed while in place in the uterus.

These and other objects and advantages of the present invention will be apparent from a review of the following specification, including the accompanying drawings.

SUMMARY OF THE INVENTION

In the present invention, a catheter tube of about 18 inches long is employed. The catheter tube has a uterine end and a gauge end. The uterine end is covered by a flexible, limp membrane having a rigid supporting structure for maintaining its general configuration.

The uterine end of the flexible membrane has a sealable latex plug, through which a small bore needle can be inserted, for filling the catheter tube with sterile solution.

The gauge end of the catheter tube is connected to an input of a pressure transducer. The pressure transducer has a closable opening so that the sterile solution, after filling the catheter tube, can overfill the transducer. The outflow opening can then be sealed assuring that no air is in the catheter tube or transducer.

To test the operation of the catheter prior to insertion in the uterus, the uterine end of the catheter can be raised or lowered to cause an increase or decrease in pressure.

The electrical cable of the transducer is then connected to the main cable which is in turn connected to a conventional monitor such as made by Corometrics.

In an alternative embodiment, the rigid supporting member for the limp membrane may be filled with a silicone type material such as Visilox so that the tip can be connected directly to a conventional catheter tube.

In one embodiment, a limp membrane is placed across the gauge end of the transducer. During use, this membrane is supported by a rigid structure to prevent expansion. When it is desirable to zero the system while in place in the uterus, the support to the flexible membrane at the gauge end of the catheter is withdrawn, permitting the membrane to expand outwards until the pressure within the system reaches equilibrium with the outside air pressure. At this point, the electrical zero of the pressuring measuring system may be adjusted, if necessary. Once checked, the support structure is returned to place, and the system again measures intrauterine pressure.

DETAILED DESCRIPTION OF THE INVENTION

Figure 1:
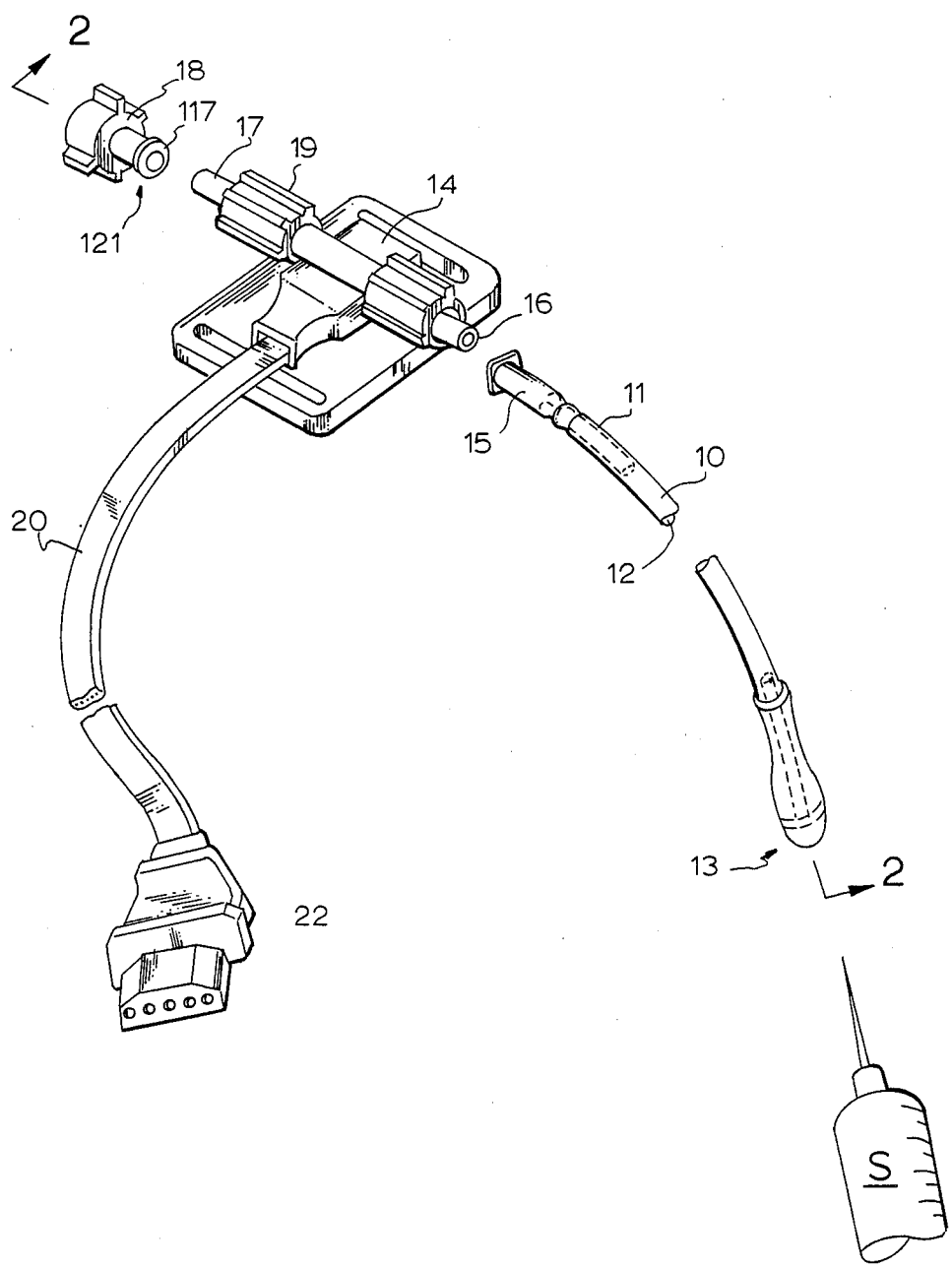
FIG. 1 is a perspective view of the improved catheter apparatus of the present invention.
Figure 2:
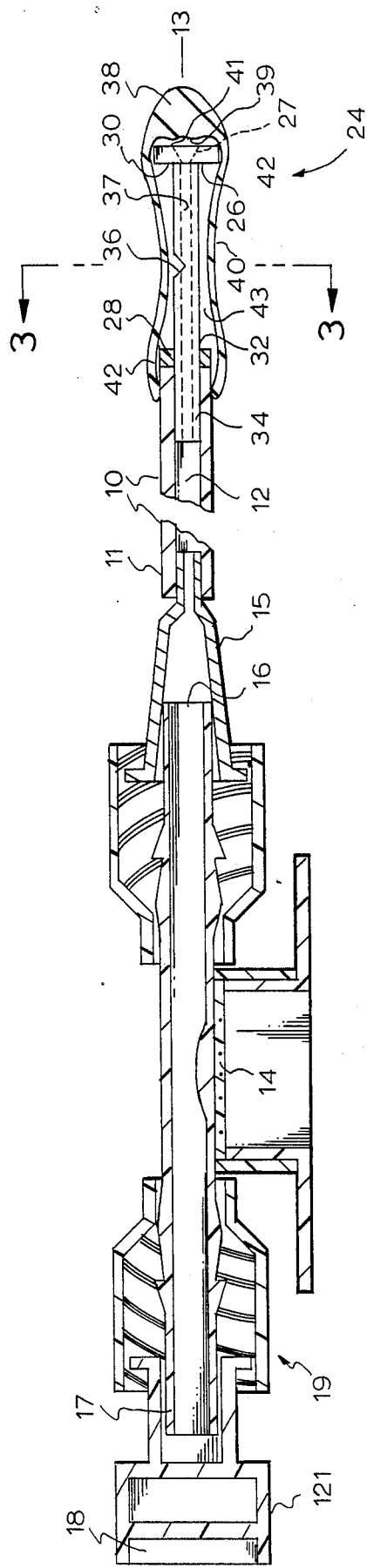
FIG. 2 is a sectional view of the catheter of FIG. 1, taken along lines 2—2.
Figure 3:
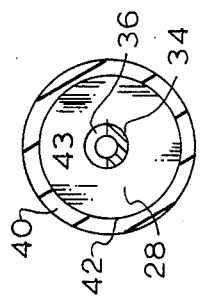
FIG. 3 is an end sectional view of the catheter of FIG. 2 taken along lines 3—3.

Referring to FIG. 1–3, the preferred embodiment of the present invention is shown.

A catheter tube 10, having a gauge end 11 and a uterine end 13, has an internal opening 12 along its entire length. The length of the catheter is approximately 18 inches, but may be as long as 2 feet. The gauge end 11 of the catheter 10 is connected by adapter 15 to the input 16 of a pressure sensing means 14. The pressure sensing means 14 has a second opening 17 closable by a cap assembly 121 and a threaded member 19 for receiving a control valve 117.

The pressure sensing means has an electrical output cable 20 having an electrical plug 22 at its end. The length of the electrical output cable 20 is approximately 7 (seven) inches. The plug 22 is designed to be attached to a main cable not shown, which is in turn connected to an electrical monitoring system.

The uterine end 13 of the catheter tube 10 is connected to a uterine tip assembly 24. The uterine tip assembly 24 consists of a first disc 26 having an opening 30 in the center having a widened portion 27, and a second disc 28 spaced away and parallel from the center of the first disc 26, also having an opening 32 in its center. A central hollow rod 34 extends from the center of the first disc 26 to the second disc 28 and then extends approximately one-half inch through the opening 32 in the second disc 28. The outer diameter of the central hollow rod 34 is such that it forms an air tight fit in the internal opening 12 of the catheter tube 10.

The central hollow rod 34 has an opening 36 in its side wall 37 between the first disc 26 and second disc 28. A cap 38 having a semi-spherical shape is affixed to the first surface 41 of the front disc 26. In preferred embodiment a space 39 is present between the front surface 41 of the first disc 26 and the cap 38.

A flexible membrane 40 is fitted between the firs disc 26 and second disc 28. Adhesive means 42 or other attachment means attaches the flexible membrane 40 to the periphery of the first disc 26 and the second disc 28, creating a hollow chamber 43 having access only through central hollow rod 34.

In the preferred embodiment, the length of the tip assembly 24 is approximately 3 (three) inches and has a cross sectional diameter of about 3/16 inches. The diameter of the catheter tube is approximately ⅛ inches, making it quite flexible.

Figure 5:
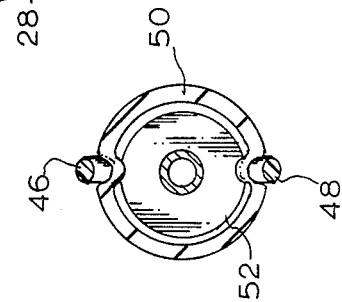
FIG. 5 is an end sectional view of FIG. 4 taken along lines 5—5 of an alternative embodiment.
Figure 4:
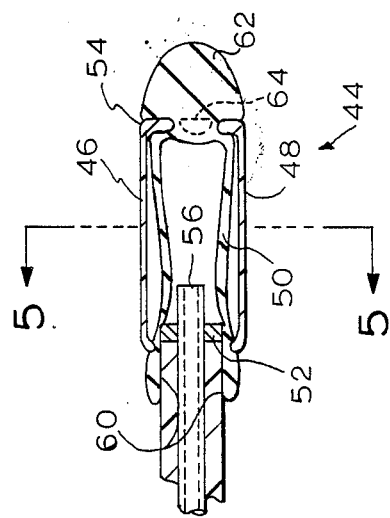
FIG. 4 is a sectional side view of a first alternative embodiment of the uterine end of the present invention.

Referring to FIG. 4 and 5, a first preferred alternative embodiment of the present invention is shown in which an exoskeleton tip assembly 44 for supporting the flexible limp membrane 50, is shown. The tip assembly 44 has two ribs 46 and 48 extending between first and second discs 54 and 52. The flexible membrane 50 is attached to the discs 52 and 54 by suitable adhesive 60. Semi-spherical cap 62 covers the first disc 54 around the periphery of disc 54. An opening 64 is located in the center of the first disc 54.

In practice, a sterilized syringe full of a saline solution is inserted through the latex cap and into the tip assembly. Solution is injected and the air is forced up the opening in the catheter tube and out of the second opening in the pressure sensing means. Before tightening the cap, the transducer end is elevated slightly to avoid trapping air bubbles and the flexible limp membrane is squeezed slightly to make sure that there is a negative pressure in the system. The cap is then tightened, sealing the system and the syringe is then removed.

Figure 6:
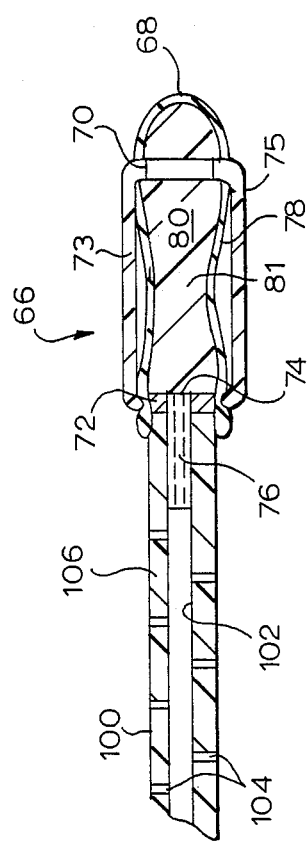
FIG. 6 is a side sectional view of a second alternative embodiment of the uterine end of the catheter.

Referring to FIG. 6 an accessory tip 66 for use with existing catheter tubes is disclosed. A semi-spherical cap 68 is attached to first disc 70 which is separated from second disc 72 by ribs 73 and 75. The second disc 72 has a central opening 74 through which extends central hollow rod 76. Flexible limp membrane 78 is adhesively attached to the periphery of the discs 70 and 72, forming an inner chamber 80. The inner chamber 80 and the central hollow rod 76 are filled with a fluid medium such as silicone based Visilox.

The central hollow rod 76 is capable of being fitted in an air tight arrangement within the internal opening 102 in catheter 100. The walls 106 of catheter tube has a series of capillary openings 104.

In operation of the device, the accessory tip 66 is fitted within the conventional intra uterine catheter, and used as present intra uterine catheters are used.

In the event of clogging of the capillary openings 104, the device will still operate.

Figure 7:
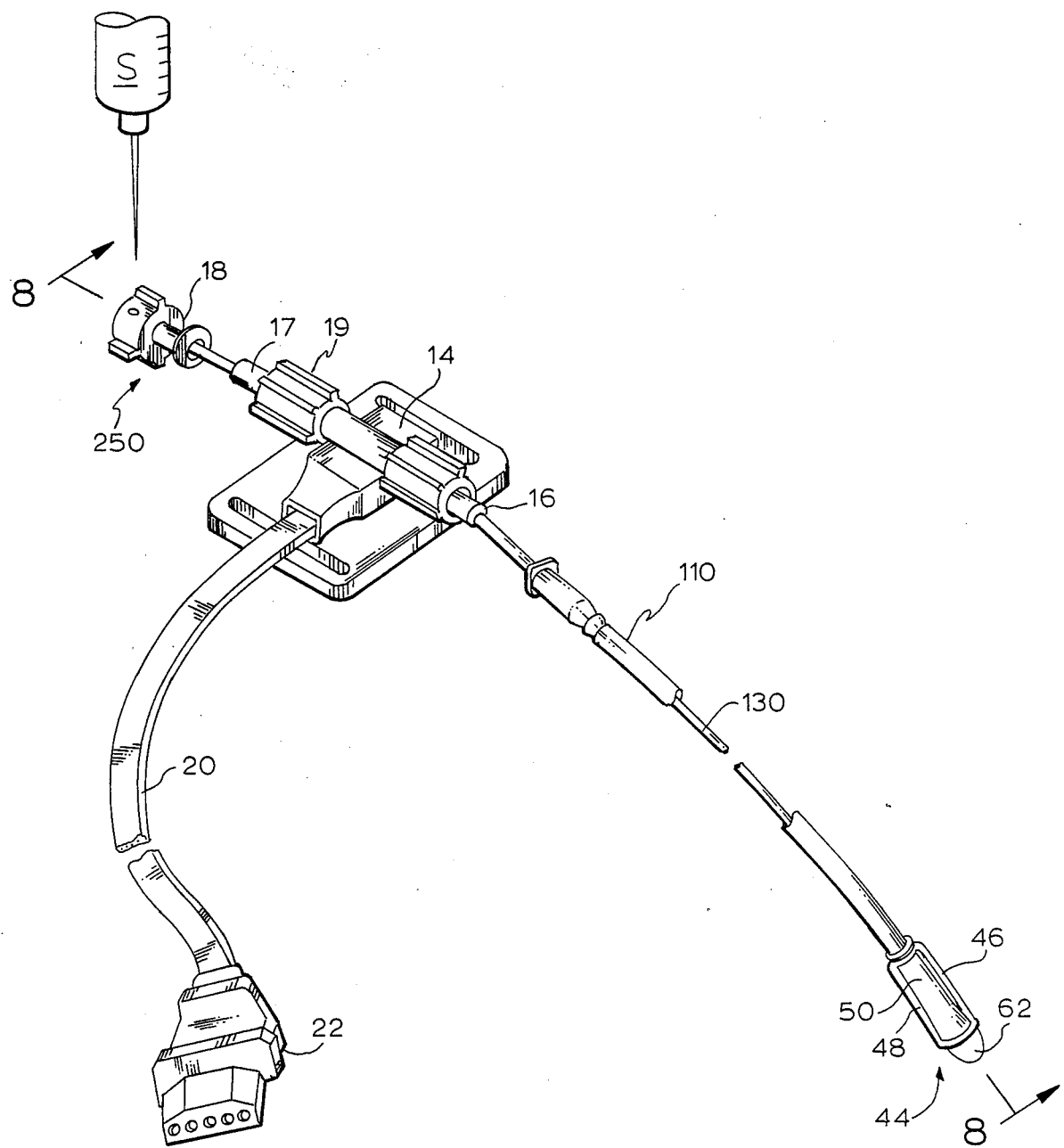
FIG. 7 is a perspective view of an alternative embodiment of the present invention using an internal fill tube.
Figure 8:
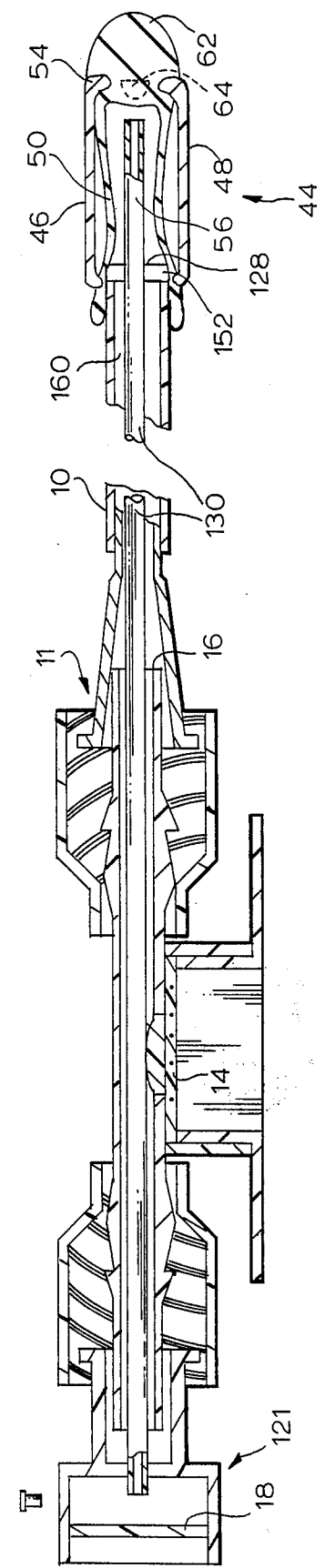
FIG. 8 is a side sectional view of the device of FIG. 7, taken along lines 8—8.

Referring to FIG. 7 and 8, another alternative embodiment of the present invention is shown.

An inner filling tube 130 is fitted within the catheter tube 110 extending through the opening 128 in disc 152 and into the chamber 160 in the tip assembly. The smaller diameter filling tube is located within the entire length of the catheter tube and permits the flow of fluid between the molded walls of the catheter tube 10 and the outside walls of the inner filling tube 130. The gauge end of the catheter tube is connected to the input 16 of the transducer 14, and the filling tube 130 is connected to cap 250 which is covered by a loose end having a latex cover 18. A sterile solution, such as water is inserted, by a syringe S, through the latex cover 18 into the filling tube 130, and then into assembly 44 and back up the catheter tube 10. When the water flows out of the opening cap 17, the syringe S is removed and the cap 250 tightened.

The latex material 18 is such that it is essentially self-sealing after the removal of the small gauge needle of the syringe.

Figure 9:
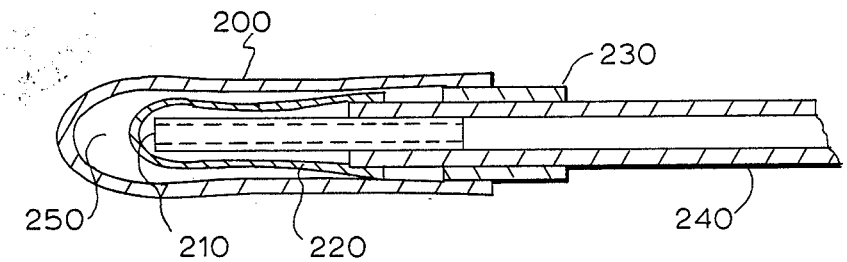
FIG. 9 is a side sectional view of a protective cap used during sterilization.

Referring to FIG. 9, a protective cap is shown for protecting the tip during shelf storage as well as during sterilization. The cap 200 fits over the entire tip 210 fitting snugly so that there is little space between the flexible membrane 220 and the inside wall of the cap 200. A latex seal 230 surrounds the catheter 240 and forms a sealed enclosure 250. The protective cap 200 prevents the flexible membrane from expanding excessively during sterilization and bursting like a balloon. Sterilization frequently occurs under reduced atmospheres so that fluids may boil and expand within the catheter. The protective cap limits the expansion of the flexible membrane.

Additionally, a water soluble gel, such as compositions of glycerine and methylcellulose, may be inserted within the cap enclosure 250 to protect the flexible membrane material during storage and sterilization.

Figure 10A:
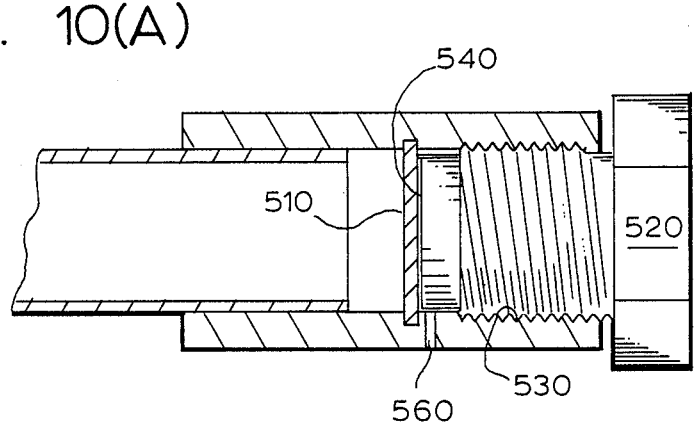
FIG. 10A is a section view of the zeroing apparatus in non zeroing position.
Figure 10B:
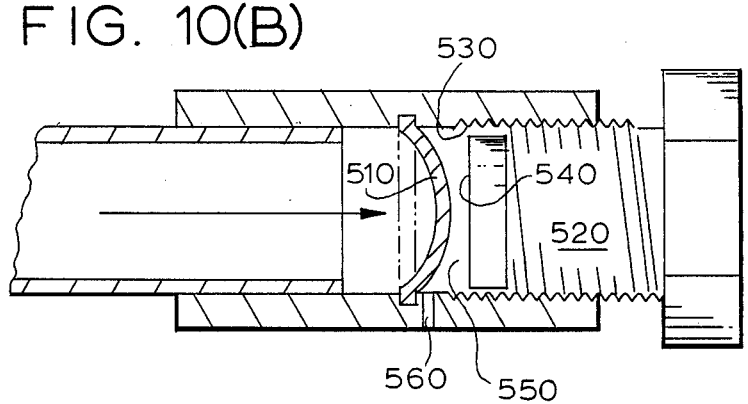
FIG. 10B is a section view of the zeroing apparatus in zeroing position.

Referring to FIG. 10A and 10B, an alternative embodiment of the present invention is shown which permits zeroing of the intra uterine catheter system when it is in place in the uterus.

When unusual pressure recordings are made by an intra-uterine pressure measuring system, it is important to determine if they are covered by actual biologic changes or caused by electrical malfunction. The electrical system is checked by reducing the intra uterine pressure until it is in equilibrium with atmospheric pressure and adjusting the electrical zero of the system if it is necessary. When the electrical zero of the system is checked and the system closed, any pressure recordings are caused by biologic changes.

The ability to check the electrical zero of the system is still important, for in certain medical situations such as Abruptio Placenta and toxemia of pregnancy the tomis of the uterine contractors may be higher than normal, thus providing early indication of a abnormal medical situation. Without a method of checking the electrical performance of the pressure measuring system it would not be possible to determine the source of an unusual pressure recording.

Referring to FIG. 10A, a cross section of the zeroing system 500 is shown.

The structure is essentially the same as that of cap 18 discussed above with the exception of the added rear structure used for zeroing the system in place. A limp membrane 510 is fitted across the inside diameter of the transducer opening. The limp membrane 510 is preferably made of latex, although other flexible membrane materials may be used which have little energy transference. A threaded plug 520 engages a corresponding threaded tubular portion 530 behind the flexible membrane 510. The front face 540 of the threaded plug 520 is essentially flat and is capable of being advanced until it rests flush against the flexible membrane 510.

The threads are loosely fitted so the chamber 550 formed between the front face 540 of the threaded plug 520 and the flexible membrane 510 is essentially open to the air. This may be achieved also by use of an air bleed hole 560 which will admit air to the chamber 550.

Referring to FIG. 10A and 10B the operation of the device is shown. The system is installed in place in the manner indicated previously. If it is desired to check the zero of the system, the threaded plug 520 is rotated from its position shown in FIG. 10A to the position shown in FIG. 10B. As indicated in FIG. 10B the limp membrane, no longer supported by the front face 540 of the threaded plug 520, is now free to expand due to the pressure exerted on the limp membrane 510 by the fluid in the catheter and the pressure from the intrauterine space.

The limp membrane 510 will continue to expand until an equilibrium is reached between the pressure inside the catheter and the outside pressure, namely air. Thus, the system is essentially opened to air with the threaded plug 520 retracted away from the flexible membrane 510. It is recognized that there is a slight amount of energy stored in the flexible membrane, but this energy may be disregarded as insignificant.

While the present invention has been described with regards to particular embodiments, it is recognized that additional variations of the present invention may be devised without departing from the inventive concept.

What is claimed is:

1. An intrauterine catheter for measuring intrauterine pressure comprising:
   (a) an elongated flexible catheter tube having a uterine end and a gauge end for providing a liquid coupling from a uterus to a suitable pressure measuring device;
   (b) a flexible membrane member enclosing the uterine end of said flexible catheter tube, said flexible membrane member includes a rigid structure for supporting at least a portion of said membrane member;

(c) a hollow filling tube fitted within said catheter tube extending to substantially the uterine end of the said catheter tube;
(d) a pressure measuring device having a first input and a second input, said pressure measuring device connected to said gauge end of said catheter tube.

2. The apparatus of claim 1 in which said filling tube extends through substantially the entire length of said catheter tube.

3. The apparatus of claim 1 in which said flexible membrane member is made from latex.

4. The apparatus of claim 1 in which said hollow filling tube extends through a chamber in said pressure measuring device and is accessible for filling through the second input in said pressure measuring device.

5. The apparatus of claim 4 in which said second input has a cap covering said second input, said cap capable of being moved between a first open position and a second closed position so that when said cap is open fluid and air may flow through the second input and when in said closed position fluid or air may not flow through the second input.

6. The apparatus of claim 5 in which said cap is covered by a self-sealing material capable of being penetrated by the needle of a syringe.

7. The apparatus of claim 1, in which said catheter tube is less than two feet long.

8. The apparatus of claim 1 in which said pressure measuring device has an electrical output cable less than one (1) foot long.

9. An intrauterine catheter comprising:
(a) a hollow catheter tube, said catheter tube having a uterine end and a gauge end;
(b) A tip assembly, said tip assembly comprising a first flexible membrane covering the uterine end of the catheter tube, said first flexible membrane having support means for supporting said first flexible membrane; and
(c) said gauge end is covered by a second flexible membrane, said second flexible membrane being pressed against a movable plug member, said plug member being movable from a first position against said second membrane to a second position away from said second flexible membrane; and a means for exposing said second flexible membrane to air pressure when said movable plug member is moved to its second position.

10. The apparatus of claim 9 in which said support means comprises at least one internal rigid member.

11. The apparatus of claim 10, in which said support means comprises a rigid hollow member having an opening therein to the interior of said membrane.

12. The apparatus of claim 9 in which said support means comprises an external rigid structure external of said flexible membrane.

13. The apparatus of claim 9, in which a portion of said tip assembly comprises a self-sealing plug.

14. The apparatus of claim 13 in which said self-sealing plug is made from latex.

15. The apparatus of claim 9, in which said gauge end of said catheter tube is connected to a pressure sensing means having an electrical output cable.

16. The apparatus of claim 15 in which said electrical output cable has means for connection to a second electrical cable.

17. The apparatus of claim 16 in which said electrical output cable is less than one (1) foot long.

18. The apparatus of claim 9 in which said catheter tube is less than three feet long.

19. An internal uterine catheter assembly for attachment to a catheter tube comprising (a) a flexible membrane forming an enclosed chamber, said flexible membrane having a rigid support means for supporting said flexible membrane;
(b) means for attachment of said assembly to a catheter tube; and
(c) said assembly including a self-sealing plug capable of being penetrated by the needle of a syringe so as to permit a fluid to be inserted by a syringe into said tubular catheter.

20. The apparatus of claim 19 in which said support means comprises a rigid internal member.

21. The apparatus of claim 19 in which said support means comprises at least one rigid external member.

22. The apparatus of claim 19 in which said plug is made of latex.

23. The apparatus of claim 19 in which said chamber is filled with Visilox.

24. The apparatus of claim 19 in which said chamber is filled with a semi-solid non-compressible material.

25. The apparatus of claim 19 in which said chamber is filled with a fluid.

26. An intrauterine catheter for measuring intrauterine pressure comprising:
(a) an elongated flexible catheter tube having a uterine end and a gauge end for providing a liquid coupling from a uterus to a suitable pressure measuring device;
(b) a flexible membrane member enclosing the uterine end of said flexible catheter tube, said flexible membrane member includes a rigid structure for supporting at least a portion of said membrane member;
(c) a hollow filling tube fitted within said catheter tube extending to substantially the uterine end of said catheter tube;
(d) a pressure measuring device having a first input and a second input, said second input has a cap covering said second input, said cap capable of being moved between a first open position and a second closed position so that when the cap is open fluid and air may flow through the second input and when in said closed position fluid or air may flow through the second input, said pressure measuring device connected to said gauge end of said catheter tube.

27. The apparatus of claim 26 in which said cap is covered by a self-sealing material capable of being penetrated by the needle of a syringe.

28. An intrauterine catheter comprising:
(a) a hollow catheter tube, said catheter tube having a uterine end and a gauge end, said gauge end is covered by a flexible membrane, said flexible membrane being pressed against a movable plug member, said plug member being movable from a first position against said membrane to a second position away from said flexible membrane; and a means for exposing said flexible membrane to air pressure when said movable plug member is moved to its second position; and
(b) a tip assembly, said tip assembly comprising a flexible membrane covering the uterine end of the catheter tube, said flexible membrane having support means for supporting said flexible membrane.

29. The apparatus of claim 28 in which said means for exposing said membrane to air is an opening.

30. The apparatus of claim 29 in which said catheter tube has capillary openings in its side walls.

31. The apparatus of claim 28 in which said means for exposing said membrane to air is an opening.

32. The apparatus of claim 31 in which said catheter tube has capillary openings in its side walls.

* * * * *